US009970930B2

(12) United States Patent
Campbell et al.

(10) Patent No.: US 9,970,930 B2
(45) Date of Patent: May 15, 2018

(54) DRUG DISCOVERY AND PROTEIN-PROTEIN INTERACTION ASSAY USING FLUORESCENT PROTEIN EXCHANGE

(71) Applicant: The Governors of the University of Alberta, Edmonton (CA)

(72) Inventors: Robert E. Campbell, Edmonton (CA); Yidan Ding, Edmonton (CA); Spencer Alford, Stanford, CA (US); Jhon Ralph Enterina, Edmonton (CA); Tiffany Yan Lai, Edmonton (CA)

(73) Assignee: The Governors of the University of Alberta, Edmonton, AB (CA)

( * ) Notice: Subject to any disclaimer, the term of this patent is extended or adjusted under 35 U.S.C. 154(b) by 0 days. days.

(21) Appl. No.: 14/705,213

(22) Filed: May 6, 2015

(65) Prior Publication Data

US 2015/0323544 A1    Nov. 12, 2015

Related U.S. Application Data

(60) Provisional application No. 61/991,178, filed on May 9, 2014.

(30) Foreign Application Priority Data

May 9, 2014    (CA) ..................... 2851568

(51) Int. Cl.
*G01N 33/68*    (2006.01)
*G01N 33/542*    (2006.01)

(52) U.S. Cl.
CPC .......... *G01N 33/542* (2013.01); *G01N 33/68* (2013.01); *G01N 33/6845* (2013.01)

(58) Field of Classification Search
CPC .. G01N 33/542; G01N 33/6845; G01N 33/53; A61B 5/00
See application file for complete search history.

(56) References Cited

U.S. PATENT DOCUMENTS

| | | |
|---|---|---|
| 6,294,330 B1 | 9/2001 | Michnick et al. |
| 6,828,099 B2 | 12/2004 | Michnick et al. |
| 6,897,017 B1 | 5/2005 | Michnick et al. |
| 7,166,424 B2 | 1/2007 | Michnick et al. |
| 7,666,606 B2 | 2/2010 | Waldo |
| 8,426,153 B2 | 4/2013 | Berget |

OTHER PUBLICATIONS

A printout retrieved from http://www.labcanada.com/laboratory/fluorescent-colour-changing-proteins-shed-light-on-inner-workings-of-live-cells/1003451926/ on Aug. 12, 2016.*
User's Guide to Alpha Assays Protein:Protein Interactions—PerkinElmer, May 2011, p. 27, retrieved from https://www.perkinelmer.com/lab-solutions/.../docs/GDE_ Alphatech.pdf on Aug. 12, 2016.*
A printout retrieved from https://en.wikipedia.org/wiki/Peptide on Aug. 12, 2016.*
Alford, Spencer C. et al., "A Fluorogenic Red Fluorescent Protein Heterodimer," Chem & Bio 19, 353-360, Mar. 2012.
Alford, Spencer C. et al., "Dimerization-Dependent Green and Yellow Fluorescent Proteins," ACS Synth. Biol. Aug. 2012, 1, 569-575.
Ding et al., (Jan. 2015) "Ratiometric biosensors based on dimerization-dependent fluorescent protein exchange," Nature Methods, vol. 12 No. 3: 195-199 with 3 pages of online methods.
Ding et al., "Ratiometric biosensors based on dimerization-dependent fluorescent protein exchange," Supplemental Information, Nature Methods, vol. 12 No. 3, Jan. 2015; 21 pages.
Alford, Spencer C. et al., Supplemental Information for "A Fluorogenic Red Fluorescent Protein Heterodimer," Chem & Bio 19, 353-360, Mar. 2012 available on-line at the web site www.sciencedirect.com/science/article/pii/S1074552112000191.
Alford, Spencer C. et al., Supplemental Information for "Dimerization-Dependent Green and Yellow Fluorescent Proteins," ACS Synth. Biol. Aug. 2012, 1, 569-575 available on line at the web site pubs.acs.org/doi/suppl/10.1021/sb300050j.
Fukuda, M., Gotoh, I., Gotoh, Y. & Nishida, E. "Cytoplasmic localization of mitogen-activated protein kinase kinase directed by its NH2-terminal, leucine-rich short amino acid sequence, which acts as a nuclear export signal." J Biol Chem 271, 20024-20028 (1996).
Kalderon, D., Roberts, B.L., Richardson, W.D. & Smith, A.E."A short amino acid sequence able to specify nuclear location". Cell 39, 499-509 (1984).
Luo, K.Q., Yu, V.C., Pu, Y., and Chang, D.C. "Measuring dynamics of caspase-8 activation in a single living HeLa cell during TNFalpha-induced apoptosis." Biochemical and Biophysical Research Communications 304 (2003) 217-222.
Porę ba, M., Stróżyk, A., Salvesen, G.S., and Drąg, M. "Caspase Substrates and Inhibitors". Cold Spring Harb Perspect Biol 2013;5:a008680, published in advance Jun. 2013.
Wen, W., Meinkotht, J.L., Tsien, R.Y. & Taylor, S.S."Identification of a signal for rapid export of proteins from the nucleus." Cell 82, 463-473 (1995).
Xu, X. et al. "Detection of programmed cell death using fluorescence energy transfer". Nucleic Acids Res. 26, 2034-2035 (1998).

* cited by examiner

*Primary Examiner* — Galina Yakovleva
(74) *Attorney, Agent, or Firm* — Lathrop Gage LLP

(57) ABSTRACT

A novel assay for determining a molecular process using a fluorescent protein exchange assay, and a composition for use thereof, are provided. The assay provides first and second signalling proteins and an exchange protein, wherein the exchange protein interacts with the first signalling protein to form a complex, then introducing the second signalling protein, wherein in response to the molecular process, the exchange protein dissociates from the first protein and associates with the second protein. The change in signal in response to the exchange of the proteins is measured to indicate a molecular process.

8 Claims, 15 Drawing Sheets

DRUG DISCOVERY AND PROTEIN-PROTEIN INTERACTION ASSAY USING FLUORESCENT PROTEIN EXCHANGE

CROSS-REFERENCE TO RELATED APPLICATIONS

This application claims the benefit of U.S. provisional application 61/991,178, filed May 9, 2014, and of Canadian Patent Application No. 2,851,568, filed May 9, 2014, each of which applications is incorporated by reference in its entirety herein.

FIELD

The present application pertains to the field of drug discovery and protein-protein interaction assays. More particularly, the present application relates to a method of high throughput assaying of drug targets and protein-protein interactions using fluorescent protein exchange.

BACKGROUND

Proteins are the machines of life and the targets of essentially all pharmaceuticals. One of the most important properties of proteins is their ability to interact with other proteins. While numerous protein-protein interactions are critical to the function of normal healthy cells, other protein-protein interactions are associated with infectious diseases, inheritable diseases, and cancer. Identifying these disease-associated protein-protein interactions is central to the discovery of new therapeutics. Once a disease-associated protein-protein interaction has been identified, researchers can begin the process of developing a therapeutic molecule that is capable of disrupting the detrimental protein-protein interaction. This effort to develop a therapeutic molecule must be guided by an assay that allows the researchers to rapidly and effectively test candidate therapeutic molecules for their ability to disrupt the specific protein-protein interaction of interest (Michnick et al., 2007).

For both the discovery of previously unknown protein-protein interactions, as well as assays of known protein-protein interactions, cell-based assays in which the interaction of interest is associated with a change in the visible fluorescence of the cells are particularly powerful.

Fluorescence is a well understood phenomenon in which the absorbance of higher energy (more blue shifted) light by a molecular species leads to the emission of lower energy (more red shifted) light with a very short time delay (typically nanoseconds). Fluorescence is the preferred readout for cell-based assays because it is extremely sensitive, versatile, and can be implemented in minimally invasive ways.

The two main challenges of using a fluorescent cell-based assay are: 1) introducing the fluorescent molecule into a cell; and 2) making the change in fluorescence intensity or color meaningfully correlated with the protein-protein interaction or other biochemical event of interest. The first of these two challenges is most effectively addressed by using fluorescent protein (FP) technology. FPs are naturally occurring proteins that have been found in various marine organisms from phyla Cnidaria (i.e., Hydrozoan jellyfish and Anthozoan coral) (Shimomura et al., 1962; Matz et al., 1999), Chordata (i.e., lancelet) (Deheyn et al., 2007; Shaner et al., 2013), and Arthropoda (i.e., a copepod crustacean) (Masuda et al., 2006). The corresponding genes encoding these proteins have been cloned from their host organisms or resynthesized in the lab, and then extensively engineered in the laboratory to produce improved FPs for research applications in biological imaging (Campbell and Davidson, 2010). Available methods to address the second challenge, and use FPs for detecting protein-protein interactions or other biochemical processes of interest, are also known.

Methods for Detecting Protein-Protein Interactions Using Fluorescent Proteins

While the strategies for using fluorescent proteins (FPs) as markers of gene expression, protein localization, and organelle structure are well-established, current methods for converting FPs into active indicators of protein-protein interactions and biochemistry in live cells remain few in number. The two standard methods for detecting protein-protein interactions in live cells are: 1) Interaction-induced reassembly of an FP that has been genetically split into two fragments (Ghosh et al., 2000; Hu et al., 2002; Alford et al., 2012; Nyfeler et al., 2005; Kerppola, 2008); and 2) Förster resonance energy transfer (FRET) between two different hues of FP (Miyawaki et al., 1997; Xu et al., 1998). For more than a decade, both of these methods have been exploited in a variety of applications that have led to numerous important biological insights. However, taken as a group, these methods suffer from a few shortcomings. For example, FRET-based biosensors tend to have relatively small fluorescent responses and are challenging to implement with multiple fluorescent probes (Carlson and Campbell, 2009); and the slow and irreversible nature of split FP complementation means that it cannot be used to visualize reversible protein-protein interactions and may also suffer from artifacts due to the capturing of weak or transient interactions (Kodama and Hu, 2012).

Dimerization-dependent fluorescent protein (ddFP) technology was recently introduced as a versatile method that attempted to address some of the drawbacks associated with split FP reconstitution and FRET assays, while providing new opportunities for the construction of biosensors (Alford et al., 2012; Alford et al., 2012). A ddFP is a pair of quenched or non-fluorescent FP monomers that can associate to form a fluorescent heterodimer. One of the monomers ("copy A" or "fluorogenic monomer") contains a fully formed chromophore that is quenched in the monomeric state. The second monomer ("copy B" or "dark monomer") does not form a chromophore itself and only acts to substantially increase the fluorescence of copy A upon formation of the AB heterodimer. In the green and red fluorescent versions of ddFP, the A copies are referred to as GA and RA, respectively. For both GA and RA, a corresponding B copy (i.e., GB and RB) was engineered that had been optimized with respect to formation of its respective fluorogenic heterodimer. DdFPs have been used individually as intensiometric biosensors for a variety of biochemical processes including protein-protein interaction, protease activity, and membrane-membrane proximity. (Alford et al., 2012; Alford et al., 2012). One example of a commonly used protease assay is the monitoring of caspase activity during the process of apoptosis (programmed cell death). To make indicators of protease activity, proteins were expressed as a tandem genetically fused AB heterodimer with a linker that contains a protease substrate. For example, caspase-3 activity indicators were created based on a linker containing the substrate sequence Asp-Glu-Val-Asp (DEVD, SEQ ID NO:1) (Xu et al., 1998) and green, red and yellow ddFPs (Alford et al., 2012; Alford et al., 2012). Traditionally, caspase-3 biosensors have relied on the loss of FRET that occurs when the substrate sequence linking a donor FP to an acceptor FP is cleaved by the protease of interest (Xu et al., 1998; Ai et al., 2008). One disadvantage of ddFPs relative to FRET for detecting protein-protein interactions or protein cleavage due to protease activity is that ddFPs provide an intensiometric (i.e., single color increase or decrease) fluorescence response, while FRET provides a ratiometric (i.e., color change) response. Generally speaking, ratiometric changes are more amenable to quantitative analysis.

U.S. Pat. No. 7,666,606, "Protein-protein interaction detection system using fluorescent protein microdomains" describes the use of a 'microdomain', or a peptide portion of the fluorescent protein. Other patents describing fluorescent technology include U.S. Pat. No. 7,166,424, "Fragments of fluorescent proteins for protein fragment complementation assays"; U.S. Pat. No. 8,426,153, "Linked peptides fluorogenic biosensors"; U.S. Pat. No. 6,294,330, "Protein fragment complementation assays for the detection of biological or drug interactions"; U.S. Pat. No. 6,828,099, "Protein-fragment complementation assays (PCA) for the detection of protein-protein, protein-small molecule and protein-nucleic acid interactions based on the E. Coli TEM-1 beta-lactamase."; and U.S. Pat. No. 6,897,017, "In vivo library versus library selection of optimized protein-protein interactions".

There is a need for a novel method of analyzing protein-protein interactions for facilitating high throughput assaying of drug targets.

This background information is provided for the purpose of making known information believed by the applicant to be of possible relevance to the present invention. No admission is necessarily intended, nor should be construed, that any of the preceding information constitutes prior art against the present invention.

SUMMARY

In accordance with one aspect of the present application there is provided a method of assaying a molecular process, comprising the steps of: providing an exchange protein and a first signalling protein, wherein the exchange protein interacts with the first signalling protein to form a first complex; introducing a second signalling protein, wherein in response to the molecular process, the exchange protein dissociates from the first signalling protein and associates with the second signalling protein to form a second complex; and measuring the change in signal generated, thereby assaying the molecular process.

The signalling proteins are typically fluorescent signalling proteins. In this embodiment, the assay measures a change in fluorescence, such as a green-to-red or red-to-green fluorescence change, to indicate a molecular process.

The signalling proteins can be conjugated with one or more further proteins to determine protein-protein interactions. The assay thus measures a change in signal generated on interaction of the one or more proteins.

The assay can be used to measure the activity of an enzyme, for example, when catalyzing the interaction between the proteins. The molecular process can include a loss of the protein-protein interaction or the physical connection.

The assay can be used to determine molecular events in the cell. These molecular events can include various protein-protein interactions or enzyme catalyzing reactions, for example. These events can take place in the cytoplasm or nucleus. The change in signal can include a change in fluorescence intensity and/or a change in subcellular localization.

The signalling proteins may be conjugated with one or more further proteins. These further proteins may interact with each other, or dissociate from each other, thereby changing the signal.

In accordance with another aspect there is provided a composition for detecting a molecular process, the composition comprising a first protein, a second protein, and an exchange protein, the exchange protein for interacting with either the first protein to form a first complex, or with the second protein to form a second complex, wherein when the exchange protein dissociates from the first protein to associate with the second protein, a change in signal is produced, thereby indicating the molecular process. The composition can be used in a cell to detect molecular events therein. The signalling proteins can be fluorescent proteins.

The present invention also provides a kit for assaying a molecular event, the kit comprising the composition as described herein. Instructions for assaying the molecular event may also be provided. For example, the kit comprises signalling proteins which are fluorescent proteins, such as green and red florescent proteins.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION

Figure 1:
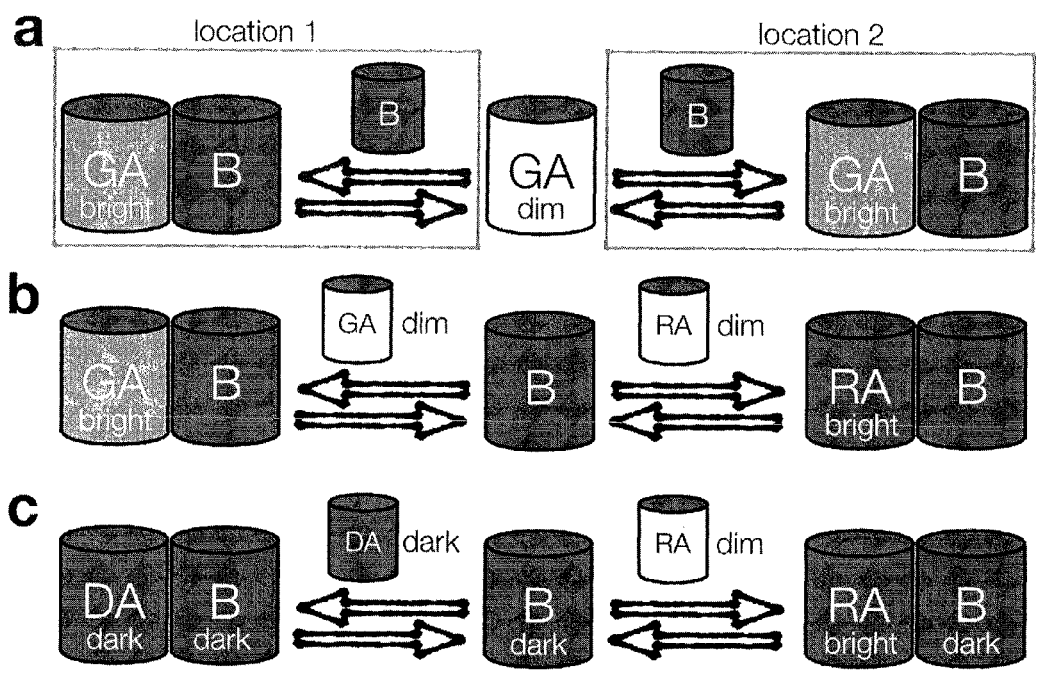
FIG. 1 shows a schematic representation of the FPX strategy.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, a "molecular event" or "molecular process" can include any biological process that can occur in or outside of a cell, including, but not limited to, protein-protein interaction or dissociation, enzyme catalyzing, signal transduction, etc., for example.

As used herein, a "signalling protein" is a protein that generates a signal, such as, for example, a fluorescent signal. The protein may generate a signal either alone or in association with another protein, or may generate a more intense signal either alone or in association with another protein, or may change or generate a change in fluorescence color either alone or in association with another protein.

As used herein, a "complex" is an entity that can include any interaction between two or more species. Non-limiting examples of "interaction" include physical association of proteins (protein-protein interaction), pi-pi interactions, or chemical bonding (e.g., hydrogen, covalent or ionic, for example).

As used herein, an "exchange" protein is a protein which dissociates from a first protein and associates with a second protein. In certain embodiments, the exchange protein preferentially binds to the first protein to form a first complex. Subsequent to a molecular event, the exchange protein disassociates from the first protein and associates with the second protein to form a second complex. Thus, the first protein "exchanges" its association between the first and second proteins. The exchange protein may be a fluorescent protein.

As used herein, a "change in signal" can indicate either a change in intensity of the level of a signal from a signalling protein or complex (such as, for example, an increase or decrease in fluorescence), or a shift in the wavelength of the emitted signal from the signalling protein or complex.

Any suitable signalling proteins can be used in the context of the present invention. It is contemplated that suitable proteins include fluorescent proteins wherein a change in binding resulting from the exchange of first and second to first and third pairings results in a change in signal, such as a fluorescent signal. In certain embodiments, there is provided a set of three signalling proteins in which the first protein can interact with the second or the third protein, but not both at the same time. A protein-protein interaction or physical connection causes the first protein to bind preferentially to the second protein, and a loss of the protein-protein interaction or a loss of the physical connection allows the first protein to bind to the third protein, with a concomitant change in signal.

This fluorescent signal can be detected using any suitable detection means known in the art, including those exemplified herein. Thus, the present composition can be used with any suitable buffer or solution that can be used to detect a change in signal, such as a fluorescent signal.

Typically, the assay can be used to detect molecular events inside or outside a cell, such as in an isolated cell or cell culture. The assay can detect events that occur in the nucleus or cytoplasm, or both. In certain embodiments, the molecular events cause a change in signal that is a change in fluorescence intensity or a change in fluorescence color, or a change in subcellular localization, i.e., translocation from the nucleus to cytoplasm or vice versa.

Development of the FPX Strategy

The development of the present Fluorescent Protein eXchange (FPX) strategy was based on the finding that the distinct versions of B optimized to pair with GA (i.e., GB) and RA (i.e., RB) can each bind to and increase the fluorescence of the "wrong" A partner. That is, GB can bind to RA and increase its fluorescence and, similarly, RB can bind to GA and increase its fluorescence. Based on this insight, the FPX indicator strategy was conceived in which fluorescent changes would be achieved through the swapping of one ddFP monomer between two appropriate ddFP binding partners that compete for binding to the first monomer. (FIG. 1). Accordingly, this design strategy requires that three different ddFP monomers be expressed in the cell.

The premise of the FPX assay is that one of the three proteins is initially bound to one of the other two proteins and, in response to a biochemical change such as a protein-protein interaction or increase in enzyme activity, is then induced to dissociate from the second protein and bind to the third protein. FIG. 1a illustrates one strategy to perform such an FPX assay; this is through an "A copy swap" in which the first protein is an A copy and the second and third proteins are B copies. In the "A copy swap" implementation of the FPX strategy, a single copy of the fluorogenic A partner (GA as represented in the scheme) can bind one of two different B versions. Although green fluorescence results in both cases, binding to one or the other copy can be distinguished by the different subcellular location of the two B copies. For example, location 1 could be the cytoplasm and location 2 could be the nucleus of a cell. In this implementation, there would be no color change upon partner exchange, since the same A copy is involved in both AB heterodimers. However, as demonstrated below, the A copy swap assay was used in conjunction with protein translocation for initial proof-of-concept demonstrations.

FIG. 1b illustrates a preferred implementation of the FPX assay referred to as the "B copy swap" in which the first protein is a B copy and the second and third proteins are different hues of the A copy (i.e., GA and RA or vice versa). In this case, the exchange of the B copy from the second to the third protein would be accompanied by a green-to-red or red-to-green color switch, depending on how the assay is configured. In this case spatial separation is not required since the swapping from the GA-bound state to the RA-bound state (or vice versa) is associated with a corresponding green-to-red (or vice versa) fluorescence color change.

FIG. 1c shows another version of the "B copy swap" implementation. An engineered dark A copy (DA) is able to compete with RA or GA for binding to the B copy. In this, a new version of the A copy has been obtained that is non fluorogenic and thus always non-fluorescent regardless of whether it is bound to B or not. This dark A (DA) copy enables B copy swap assays that involve an intensiometric increase in only a single fluorescent color. In this implementation, the association of RA and B will give a single color fluorogenic response.

FPX for Detection of Protein-Protein Interactions

Figure 2:
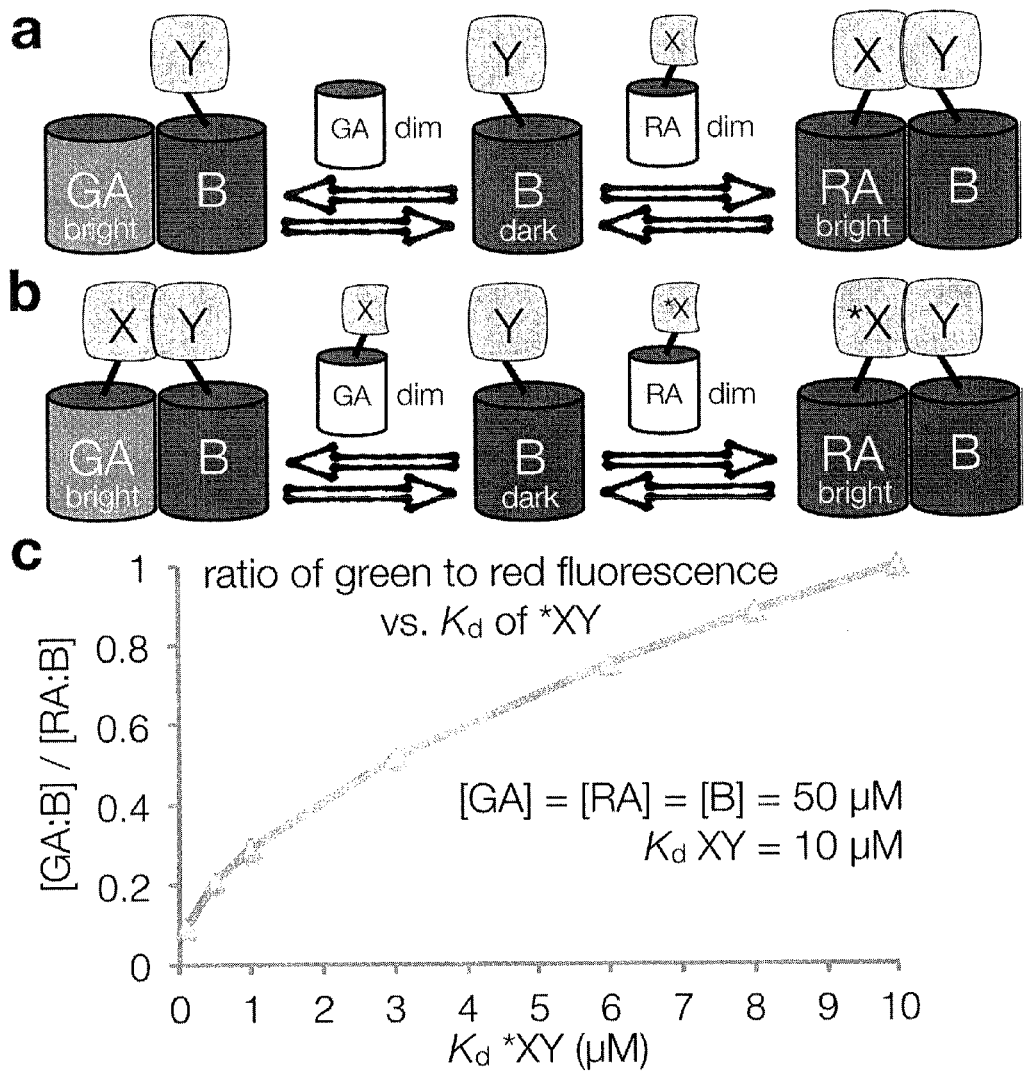
FIG. 2 shows the sensitivity to the binding of fused protein partners using FPX.

FIG. 2a shows an interaction between proteins X and Y. To use the FPX strategy (B copy swap) for detection or imaging of protein-protein interactions, free GA is co-expressed along with genetic fusions of BY and RA-X. If GA is initially present in excess it will be preferentially bound to the B copy and the ratio of red-to-green fluorescence will be very low in the absence of an interaction. However, if X and Y do interact, the ratio of red-to-green fluorescence will dramatically increase due to the high effective concentration of RA. This provides a huge ratiometric response that is much higher than those that could be obtained with FRET. Such an approach could be used for validation of particular protein-protein interactions, or genome-wide screens for novel interacting partners for a particular "bait" protein of interest. For discovery of new protein-protein interactions, the "bait" protein would be fused to B and the "prey" library fused to RA. GA would be expressed with no partner, or with a partner that has a weak interaction with the bait. Screening would be done by plate-reader assay or Fluorescence activated cell sorting (FACS) on the basis of the ratio of red-to-green fluorescence, where a higher ratio indicates a higher affinity interaction.

FPX for the Development of Inhibitors of Protein-Protein Interactions

The FPX strategy (B copy swap) can also be used to engineer protein domains or peptides that interfere with protein-protein interactions. In the schematic shown in FIG. 2b, *X is an engineered inhibitor of the X-Y interaction. To develop higher affinity genetic libraries of *X can be made using genetic randomization techniques such as error-prone PCR or saturation mutagenesis. Large libraries of variants can be screened by cell sorting and clones exhibiting the highest ratio red-to-green fluorescence identified. Such variants would be the most potent (highest affinity) inhibitors in the library.

FIG. 2c shows that modeling of this competitive binding equilibrium demonstrates that the ratio of concentrations for the two bright complexes (and thus the ratio of green and red fluorescence intensities) is exquisitely sensitive to the $K_d$ of the interacting partners. Using the measured $K_{dS}$ for the ddFPs and realistic estimates of intracellular concentrations, we determined that if $K_d$ for binding of *X to Y is a factor of 10 lower than the $K_d$ for binding of X to Y (e.g., 1 µM and 10 µM), the ratio of green-to-red fluorescence will be 3-fold lower than if the $K_{dS}$ were equivalent (e.g., 10 µM and 10 µM). High-throughput fluorescence screening systems such as plate-readers, automated microscopes, colony fluorescence imaging systems, and FACS instruments, are all extremely sensitive to even small changes in fluorescence ratio and could easily identify cells or clones that differ in ratio by only a few percent. Accordingly, the FPX strategy will enable the rapid screening of large libraries (in the range of $10^5$ or colony screening to $10^7$ for FACS) and the identification of higher affinity binding variants.

Relative to ddFP technology, two main advantages of FPX are: the ability to implement in a ratiometric format; and insensitivity to the total concentration of protein. The fact that FPX is a competitive binding assay means that it can work effectively at concentrations that are far above the $K_{dS}$ of the individual heterodimers. That is, through the whole range of intracellular concentrations (1-100 µM) of FPs typically used in live cell imaging assays, the assay should still be effective, as long as the ratio of concentrations for the three components stays constant. In contrast, the stand-alone ddFPs are greatly affected by concentration and at concentrations higher than their intrinsic $K_d$, the proteins are largely associated regardless of the interactions of their genetic fusion partners.

Figure 3:
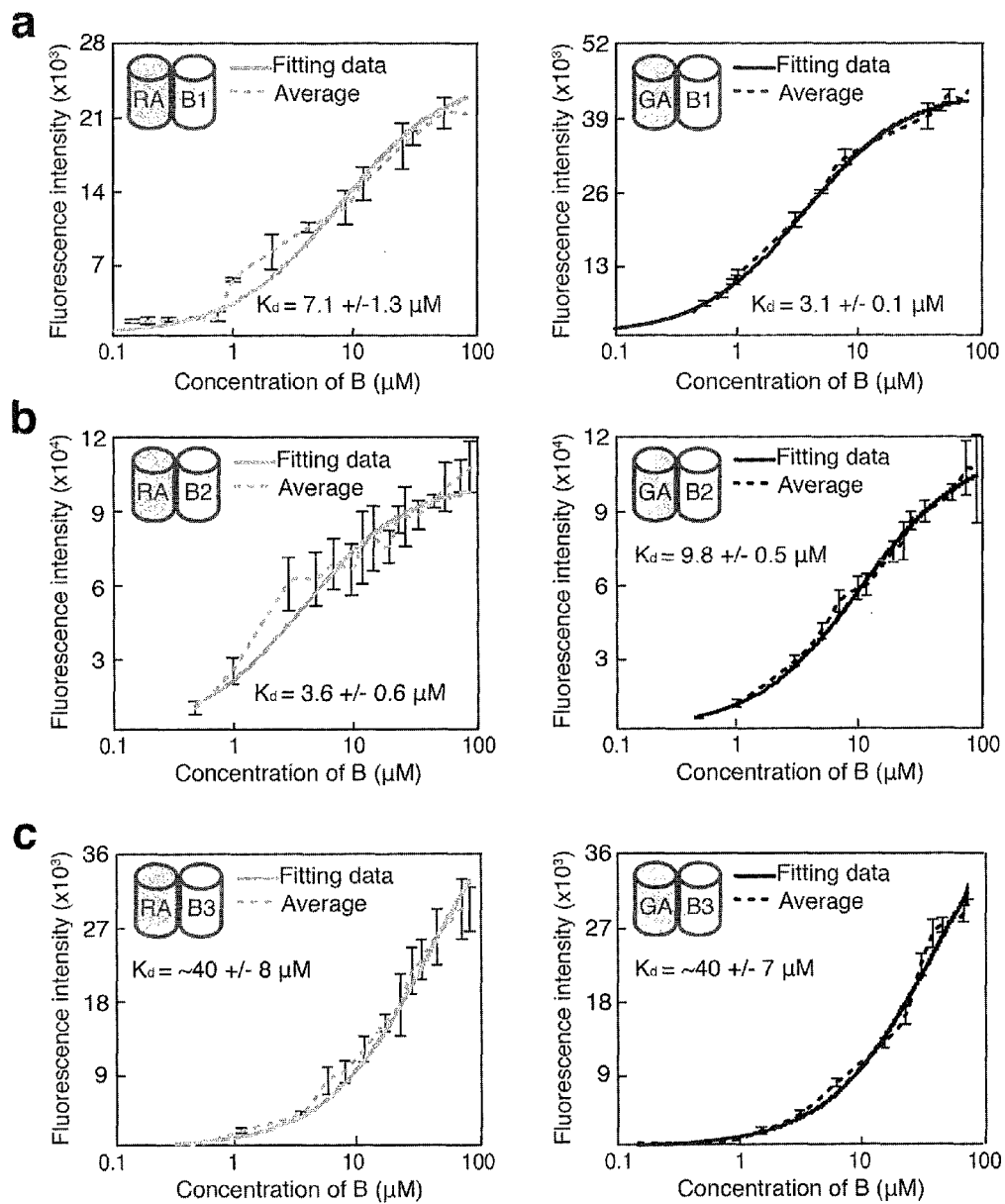
FIG. 3 shows the rescuing of fluorescence between copies.

As shown in FIG. 3, B copies with different affinities for GA and RA have been engineered. In FIG. 3a, the B copy (B1) was originally engineered to rescue the fluorescence of GA is able to rescue the fluorescence of RA. FIG. 3b shows that the B copy with the K153E mutation (B2) is also able to rescue the fluorescence of both RA and GA, albeit with slightly higher affinity for RA over GA. FIG. 3c shows that the B copy (B3) originally engineered to rescue the fluorescence of RA binds to both RA and GA with a similarly high Kd of ~40 µM.

Relative to FP FRET technology, the two main advantages of FPX are: much higher ratiometric signal changes; and the fact that the two colors can be spectrally well separated and need not have overlapping profiles. Relative to split FP technology, the three main advantages of FPX are: it is fully reversible (whereas split FP approach is irreversible); it can be used in a color-switching (ratiometric) format which is a huge advantage for quantitative applications; and the fusion proteins are highly soluble (whereas split FPs are unfolded or partially folded and poorly soluble). Any application that is possible with FRET technology or split FP technology is also possible, and typically improved, with the use of FPX technology.

EXAMPLES

Example 1: Single Color FPX Based on a Copy Swapping

Figure 4:
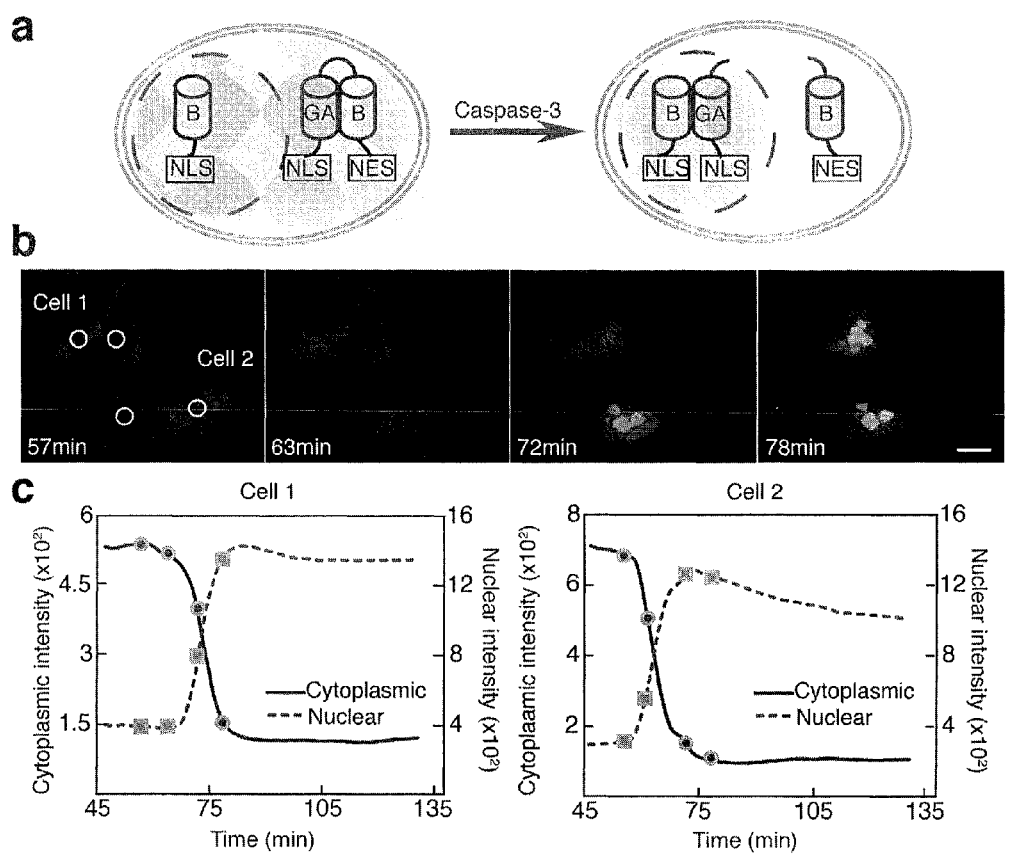
FIG. 4 shows a translocation experiment.

As a first attempt to demonstrate the FPX concept, it was investigated whether caspase-induced single color A copy swapping in live cells could be achieved. FIG. 4a shows that a green fluorescent tandem heterodimer was constructed (GA$_{NLS}$-DEVD-B$_{NES}$) in which GA plus a nuclear localization sequence (NLS) (Kalderon et al., 1984) (GA$_{NLS}$) was linked via a DEVD substrate sequence to a fusion of B plus a nuclear export signal (NES) (Wen et al., 1995) (B$_{NES}$). Here and elsewhere in this work, the general protocol for testing FPX constructs in mammalian cells involves transient transfection of HeLa cells with single or multiple pcDNA3.1(+) expression plasmids using Turbofect (Thermo Scientific). Imaging was then performed using an Axiovert 200M (Zeiss) fluorescence microscope, a laser scanning confocal LSM-700 (Zeiss) fluorescence microscope, or a Nikon Eclipse Ti fluorescence microscope.

When expressed alone, GA$^{NLS}$-DEVD-B$^{NES}$ was located in both the cytoplasm and nucleus at low expression levels and located primarily in the nucleus at high expression levels. However, when coexpressed with B$^{NLS}$ GA$^{NLS}$-DEVD-B$^{NES}$ was mainly in the cytoplasm, likely due to increased competition for binding to importins (Kakar et al., 2007). FIGS. 4b and c show that in cells where GA$^{NLS}$-DEVD-B$^{NES}$ and B$^{NLS}$ were co-expressed, activation of caspase-3 during staurosporine-induced apoptosis was associated with a loss of green fluorescence in the cytoplasm (~4-fold) and a concurrent increase in green fluorescence (~3-fold) in the nucleus. Subsequent apoptosis-associated fragmentation of the nucleus led to a decrease in the green fluorescence intensity in the nucleus. Apoptosis was initiated by treatment with 2 µM staurosporine at 24 to 48 hours post transfection. Cells were maintained in HEPES-buffered Hank's balanced salt solution (HHBSS) and subjected to imaging at 1 or 2 minute intervals for 4-6 hours. Scale bar represents 10 µM. FIG. 4c shows graphs of intensity vs. time for the cytoplasmic and nuclear ROIs indicated in FIG. 4b with markers to indicate the time points for the images. X-axis is time elapsed from 1 hour after cells were treated with staurosporine.

Figure 5:
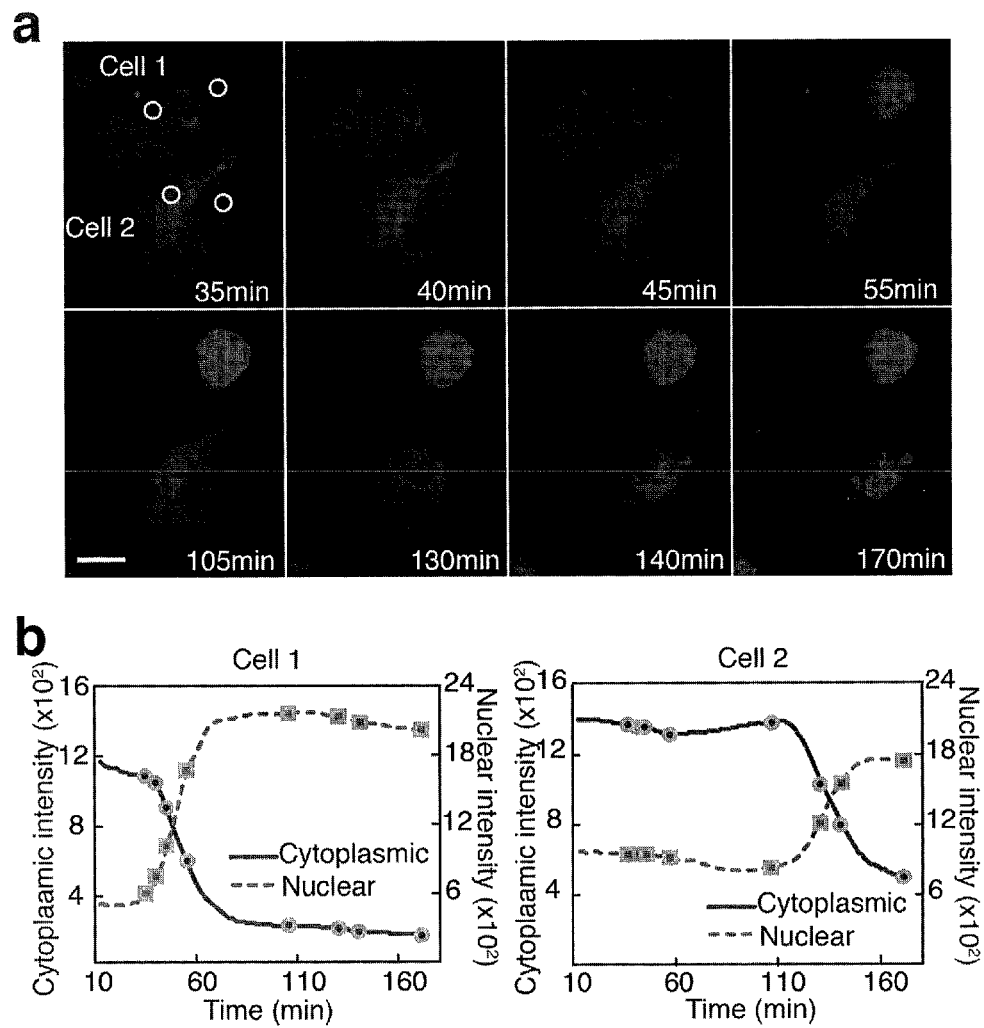
FIG. 5 shows a further translocation experiment.

FIG. 5 shows that similar results were obtained for coexpression of red fluorescent RA$^{NLS}$-DEVD-B$^{NES}$ and B$^{NLS}$. FIG. 5a shows selected frames from imaging of HeLa cells co-expressing RA$^{NLS}$-DEVD-B$^{NES}$ and B$^{NLS}$ undergoing staurosporine-induced apoptosis. Scale bar represents 10 µm. FIG. 5b shows graphs of intensity vs. time for the cytoplasmic and nuclear ROIs indicated in FIG. 5a. X-axis is time elapsed 1 h after cells were treated with staurosporine. Time points of cytoplasmic ROI and nuclear ROI corresponding to the frames in FIG. 5a are represented as circles and squares, respectively.

Example 2: Two-Color FPX Based on a Copy Swapping

Figure 6:
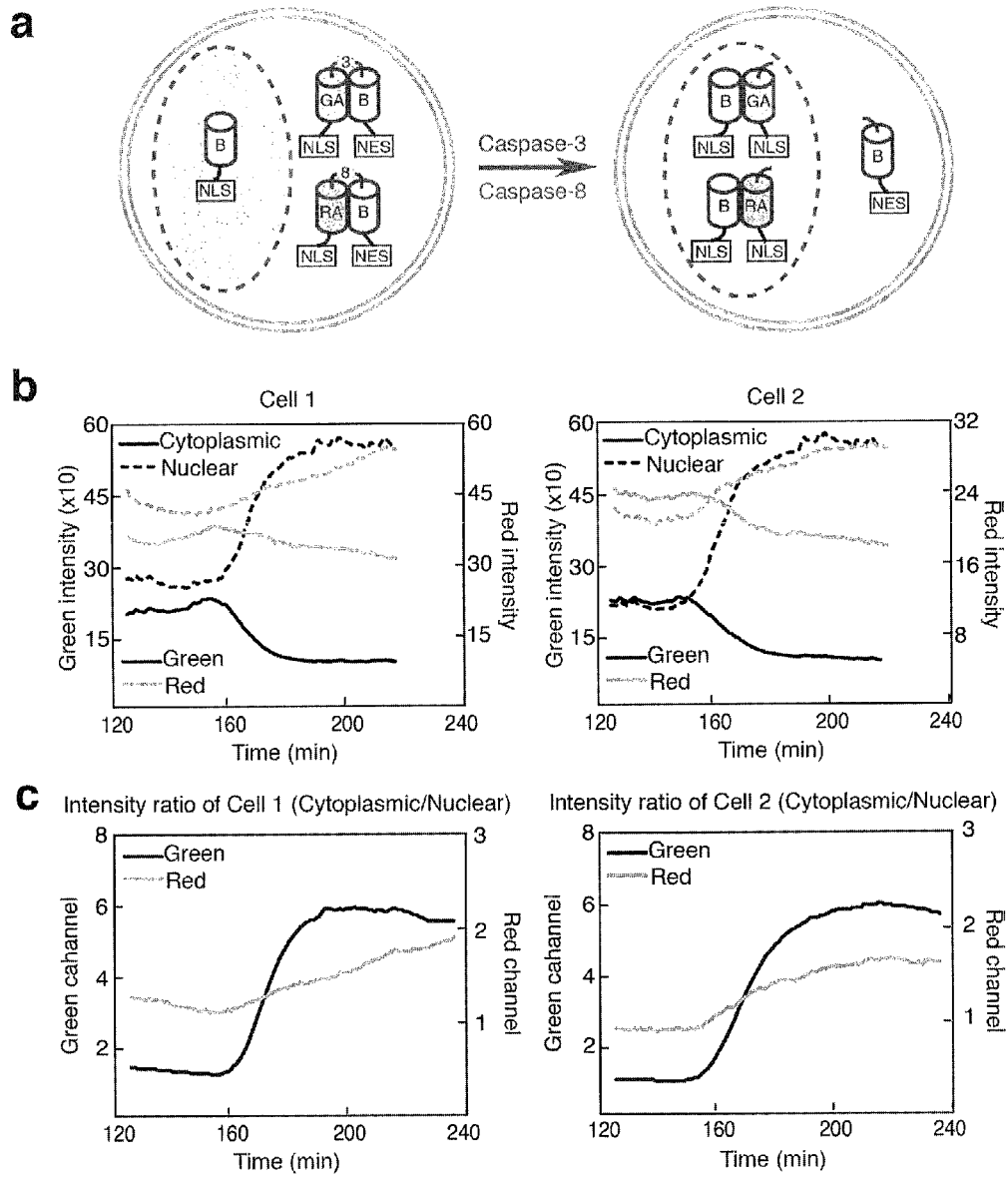
FIG. 6 shows a further translocation experiment.

Given that both the green and red fluorescent versions of the FPX caspase sensor based on A copy swapping by translocation gave robust readouts of caspase activity, two-color simultaneous detection of both caspase-3 and caspase-8 activity was attempted (illustrated in FIG. 6a). A red translocation-based caspase-8 indicator (RA$^{NLS}$-IETD-B$^{NES}$) was constructed by replacing the caspase-3 DEVD (SEQ ID NO:1) substrate sequence from RA$^{NLS}$-DEVD-B$^{NES}$ with the caspase-8 substrate sequence IETD (SEQ ID NO:2) (Luo et al., 2003). In cells co-transfected with the green caspase-3 indicator (GA$^{NLS}$-DEVD-B$^{NES}$), the red caspase-8 indicator (RA$^{NLS}$-IETD-B$^{NES}$) and the nucleus-targeted B$_{NLS}$, both green and red fluorescence was predominantly localized to the cytoplasm. FIGS. 6b and c shows that, consistent with a previous report (Kominami et al., 2012), simultaneous activation of both caspase-3 and caspase-8 during apoptosis was effectively observed, as indicated by the decrease in cytoplasmic intensity and increase in nuclear intensity in both the green and red fluorescence channels. FIG. 6b shows graphs of intensity vs. time for two-colour imaging of staurosporine-treated HeLa cells co-expressing RA$^{NLS}$-IETD-B$^{NES}$, GA$^{NLS}$-DEVD-B$^{NES}$, and B$^{NLS}$. FIG. 6c illustrates the ratios of cytoplasmic to nuclear fluorescence for the green and red channels in FIG. 6b.

Figure 7:
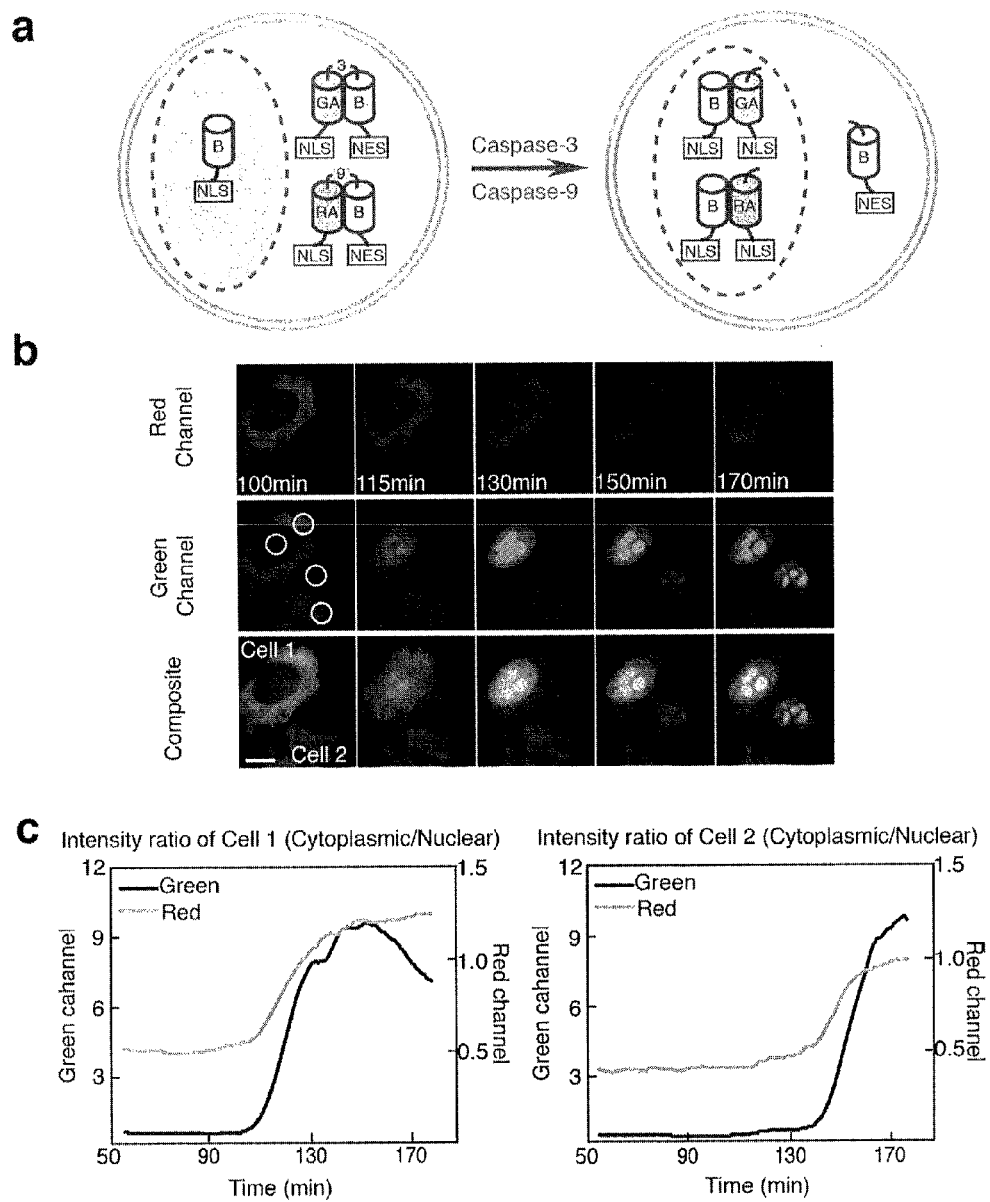
FIG. 7 shows two colour FPX with translocation partners.

FIG. 7 indicates that similar results were obtained for simultaneous monitoring of caspase-3 and caspase-9 in cells triply transfected with GANLS-DEVD-BNES, RANLS-LEHD-BNES (Thornberry et al., 1997), and BNLS. The caspase-9 substrate sequence is LEHD (SEQ ID NO:3). FIG. 7a shows a schematic illustration of monitoring both caspase-3 (green) and caspase-9 (red) activity with two different FPX constructs. FIG. 7b shows selected merged frames from two-color imaging of staurosporine-treated HeLa cells co-expressing RANLS-LEHD-BNES, GANLS-DEVD-BNES, and BNLS. Scale bar represents 10 µm. FIG. 7c shows the ratios of cytoplasmic to nuclear fluorescence intensity vs. time for the ROIs indicated in FIG. 7b.

Example 3: Color-Switch FPX Based on B Copy Swapping

Figure 8:
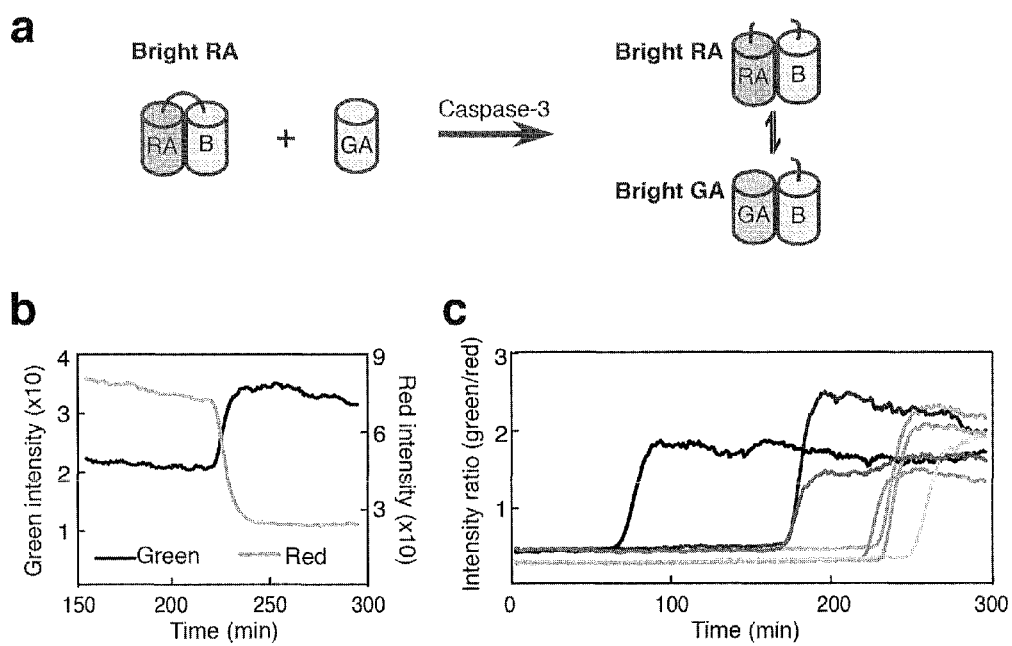
FIG. 8 shows a non-translocating red-to-green FPX for caspase activity.

In FIG. 8a, the caspase-3 sensing construct RA-DEVD-B was co-expressed along with free GA in HeLa cells with no nuclear localization or export sequences with the goal of constructing a color switch FPX sensor based on B copy swapping. The rationale for this design was that the red fluorescence would be initially bright due to the linkage of RA to the B copy. Upon cleavage the B copy would be free to bind to the free GA protein and the green fluorescence would increase as the red fluorescence decreased. FIG. 8b shows that when HeLa cells were stimulated to undergo apoptosis, a change in fluorescence through the whole cell was observed. FIG. 8c shows that increases in the green-to-red fluorescence ratio of ~5 were consistently observed. FIG. 8a shows a schematic of non-translocating FPX bio sensor for caspase-3 activity. FIG. 8b shows a curve of green and red intensity vs. time (whole cell ROI) for a HeLa cell co-expressing RA-DEVD-B and GA while undergoing apoptosis. X-axis is time elapsed since 1 h after cells were treated with staurosporine. FIG. 8c shows whole cell red-to-green intensity ratios vs. time multiple cells treated and analyzed as in FIG. 8b.

Figure 9:
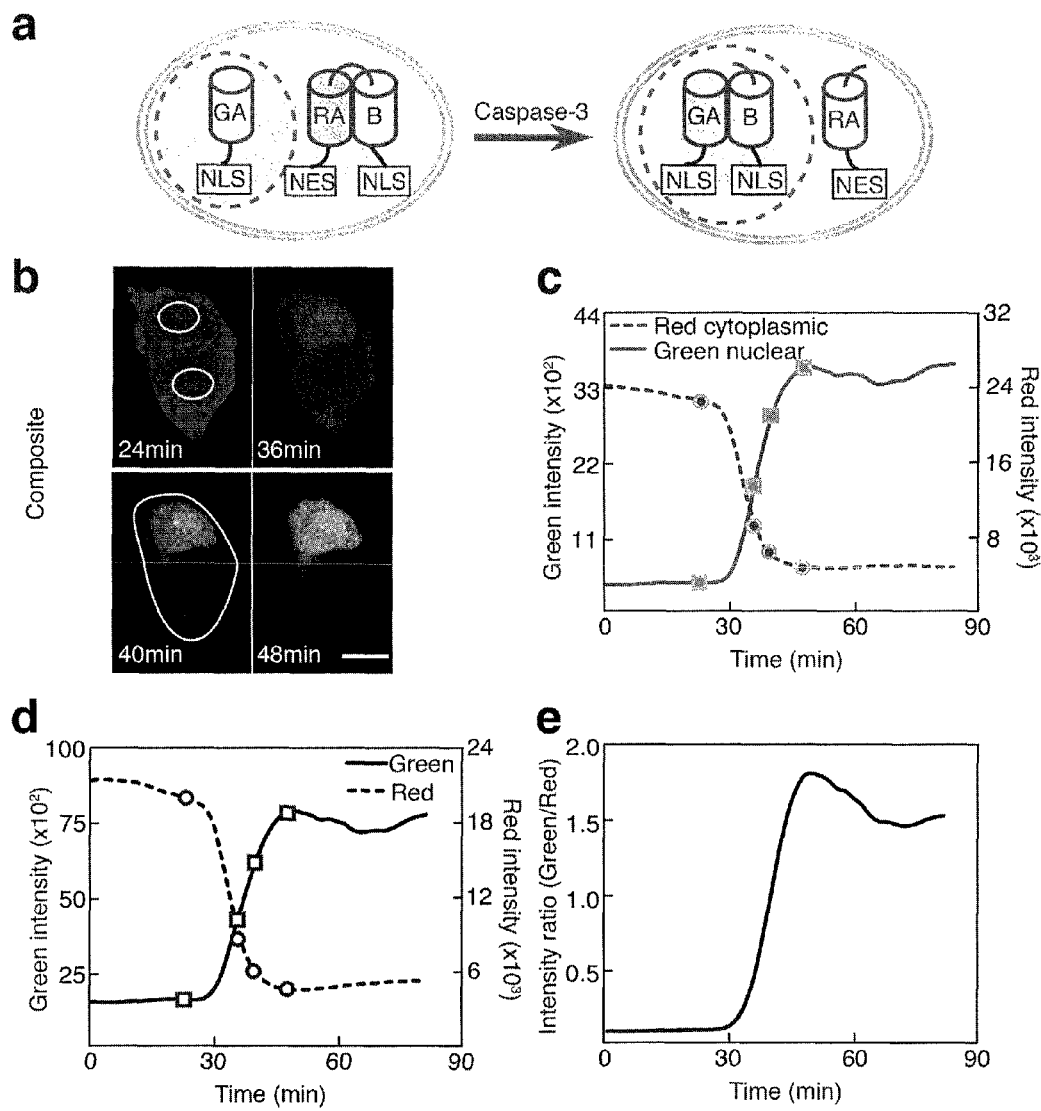
FIG. 9 shows an example of color switching translocation.

FIG. 9a shows a translocating version of this assay in which copy B would translocate into the nucleus following cleavage of a cytoplasmic A-DEVD-B construct. A red fluorescent tandem heterodimer ($^{NES}$RA-DEVD-B$^{NLS}$) was constructed and expressed in which RA plus an NES ($^{NES}$RA) was linked via the DEVD substrate to B plus an NLS (B$^{NLS}$). FIG. 9b shows selected merged frames from two-color imaging of staurosporine-treated HeLa cells co-expressing $^{NES}$RA-DEVD-B$^{NLS}$ and GA$^{NLS}$. This figure shows that when co-expressed with nuclear-localized GA (GA$^{NLS}$) $^{NES}$RA-DEVD-B$^{NLS}$ was mainly distributed in the cytoplasm. Scale bar represents 10 µm. FIG. 9c shows a graph of intensity vs. time for the ROIs indicated in the top left panel of FIG. 9b. This figure shows that activation of caspase-3 during apoptosis triggered a ~3-fold loss of red fluorescence in the cytoplasm and a ~7-fold increase in green fluorescence in the nucleus. FIG. 9d shows a graph of intensity vs. time for the whole cell ROI as indicated in the lower left panel of FIG. 9b. This figure shows that processing of the data using the whole cell as the region of interest (ROI) provided qualitatively identical results. In the graph depicted in FIG. 9e, whole cell data was also be plotted as the green-to-red intensity ratio which provided a very high signal to noise readout of caspase-3 activity.

Figure 10:
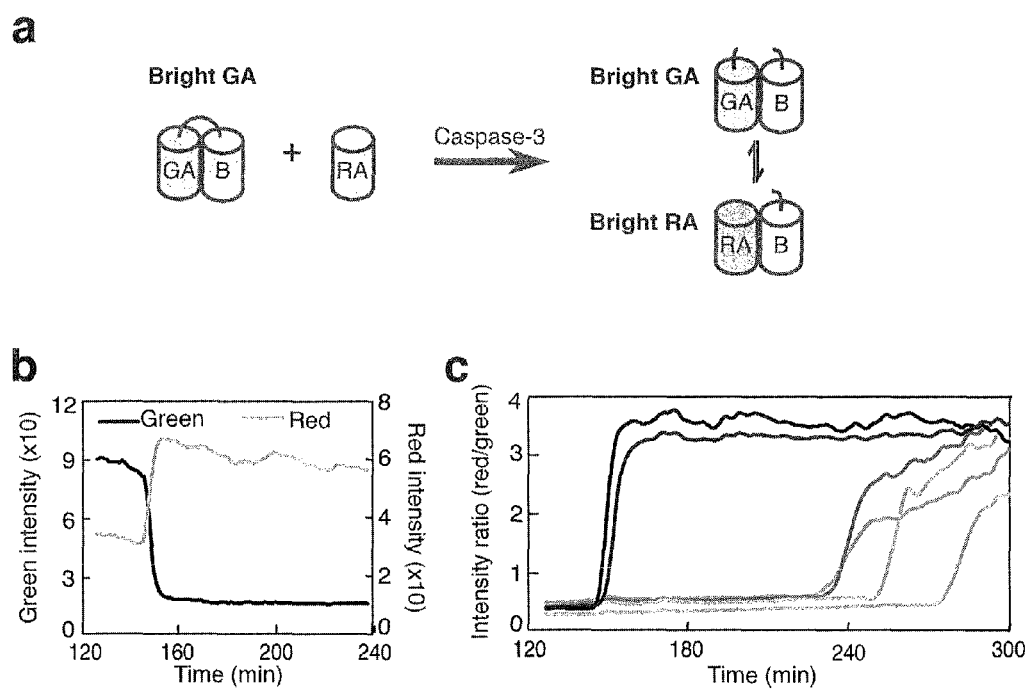
FIG. 10 shows an example of non-translocating FPX.
Figure 11:
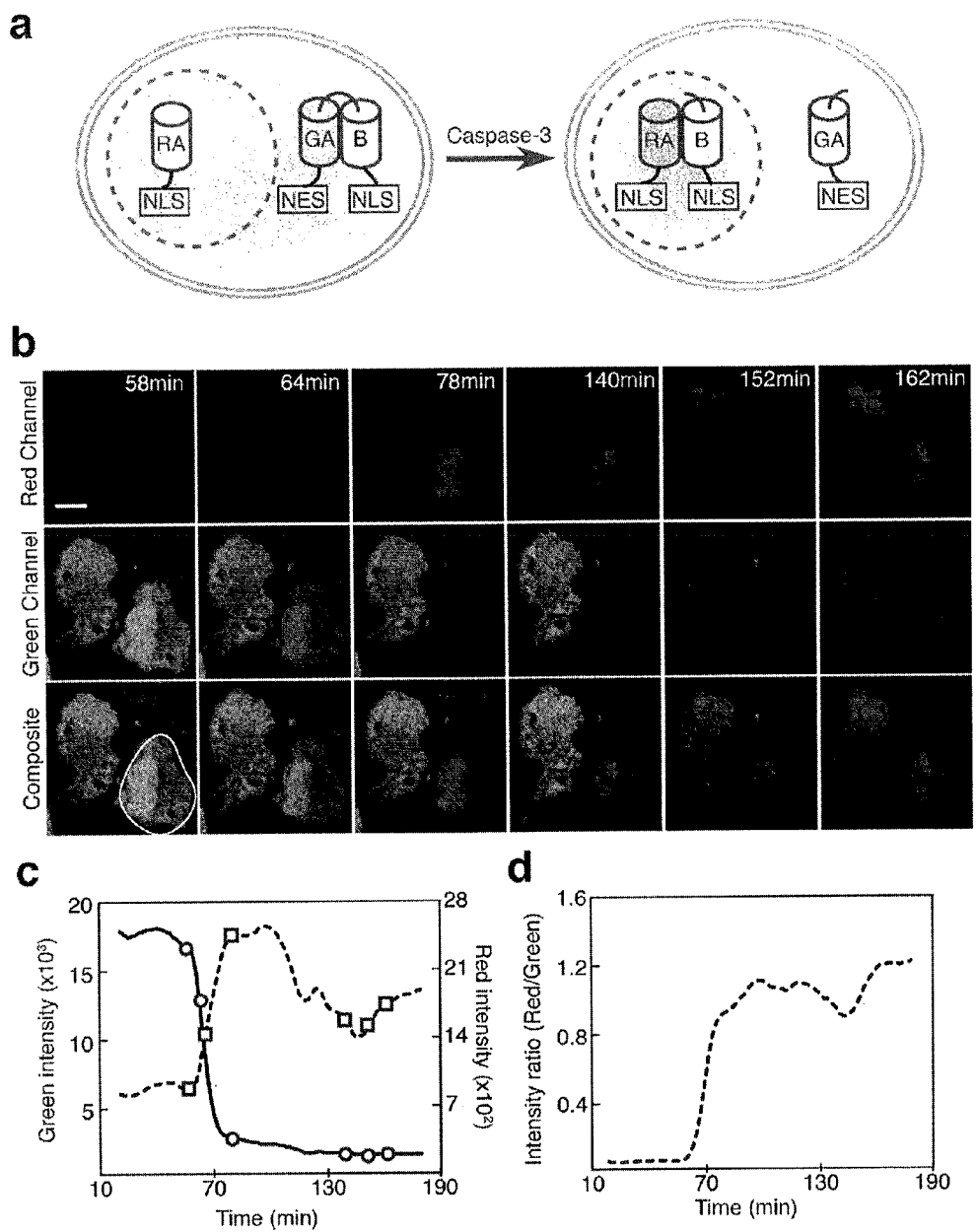
FIG. 11 shows an example of color switching translocation.

Similar results, albeit with a green-to-red color switch, were obtained with similar non-translocating (FIG. 10) and translocating (FIG. 11) constructs in which RA and GA had been switched.

FIG. 10a shows a schematic of non-translocating FPX biosensor for caspase-3 activity. FIG. 10b shows a graph of green and red intensity vs. time (whole cell ROI) for a HeLa cell co-expressing GA-DEVD-B and RA while undergoing apoptosis. X-axis is time elapsed since 1 h after cells were treated with staurosporine. FIG. 10c shows whole cell red-to-green intensity ratios vs. time multiple cells treated and analyzed as in FIG. 10b.

FIG. 11a shows a schematic of color switching translocation-based bio sensor. FIG. 11b illustrates selected frames from imaging of HeLa cells co-expressing GA$^{NES}$-DEVD-B$^{NLS}$ and RA$^{NLS}$ and undergoing apoptosis. Scale bar represents 10 µm. FIG. 11c shows a graph of whole cell intensity vs. time for the ROI indicated in lower left panel of FIG. 11b. X-axis is time elapsed since 1 h after cells were treated with staurosporine. Time points of cytoplasmic and nuclear ROIs corresponding to the frames in FIG. 11b are represented as green circles and red squares, respectively. Caspase-3 activation was associated with a ~8-fold decrease in cytoplasmic green intensity and a ~3-fold increase in nuclear red intensity. FIG. 11d shows a graph of whole cell red-to-green ratio using the data represented in FIG. 11c.

Example 4: Color-Switch FPX for Imaging a Dynamic Protein-Protein Interaction

Figure 12:
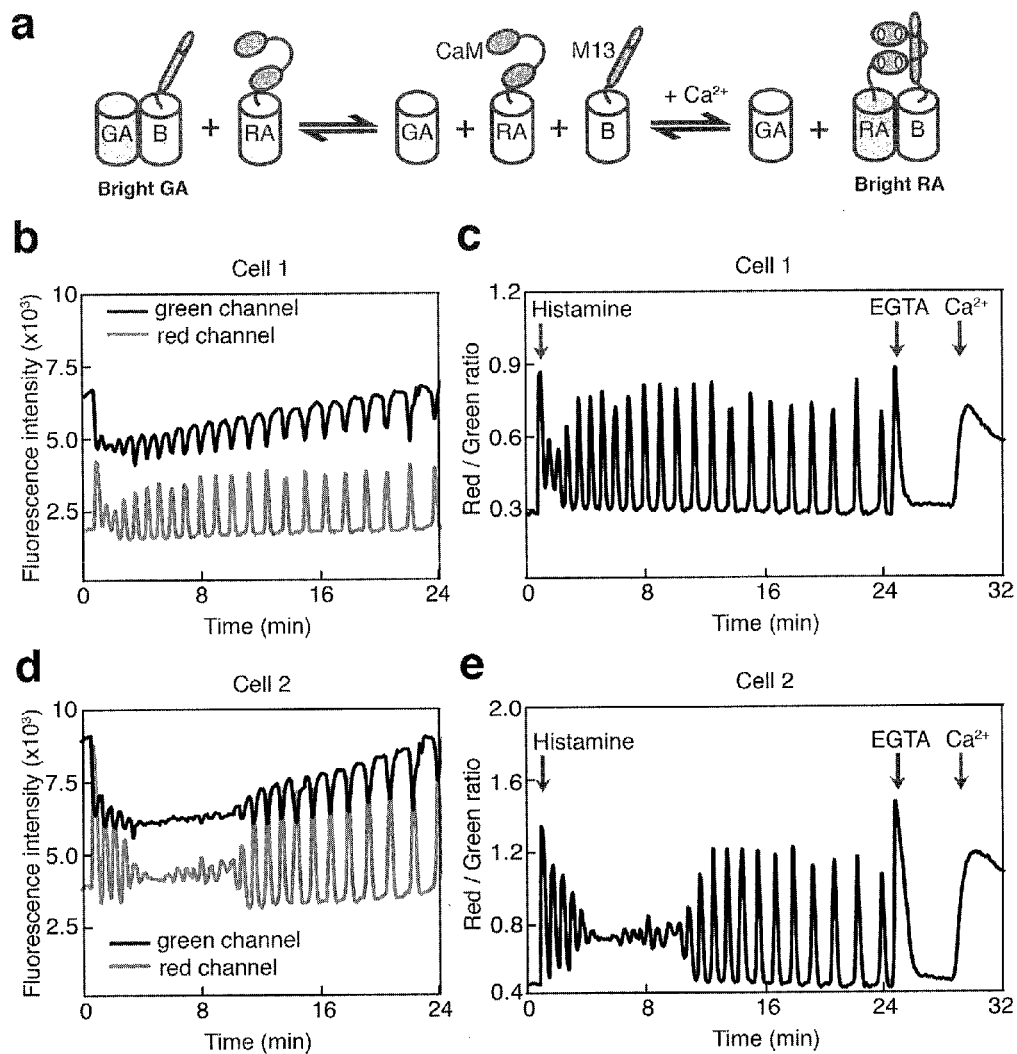
FIG. 12 shows imaging of a dynamic protein-protein interaction with colour-switch FPX.

FIG. 12a demonstrates FPX technology to image a dynamic and reversible protein-protein interaction in live cells, specifically the $Ca_{2+}$-dependent interaction of calmodulin (CaM) and the $Ca_{2+}$-CaM interacting peptide M13. In FIGS. 12b and d, HeLa cells were transfected with genes encoding B-M13, RA-CaM, and free GA and stimulated to undergo $Ca_{2+}$ oscillations by histamine treatment. Fluorescence imaging of the green and red channels was performed and it was observed that red fluorescence increased, and green fluorescence intensity decreased, in an oscillatory fashion. These oscillations are the expected result for HeLa cells treated with histamine.

FIGS. 12c and e show that while the intensity in both the green and red emission channels was quite strong, the signal-to-noise ratio of the data (i.e., the data quality) was improved by dividing the red intensity by the green intensity to provide the ratiometric signal. This result demonstrates

Example 5: Color-Switch FPX with Intramolecular B Copy Swapping

One drawback of the FPX strategy, as implemented in Examples 1 through 4, is that it requires cells to be expressed with either 2 or 3 different plasmids encoding components of the reporter system. It might be possible to combine all three components of the FPX system into a single polypeptide chain and thereby simplify the transfection procedure while also providing less cell-to-cell variability in terms of fluorescence ratios.

Figure 13:
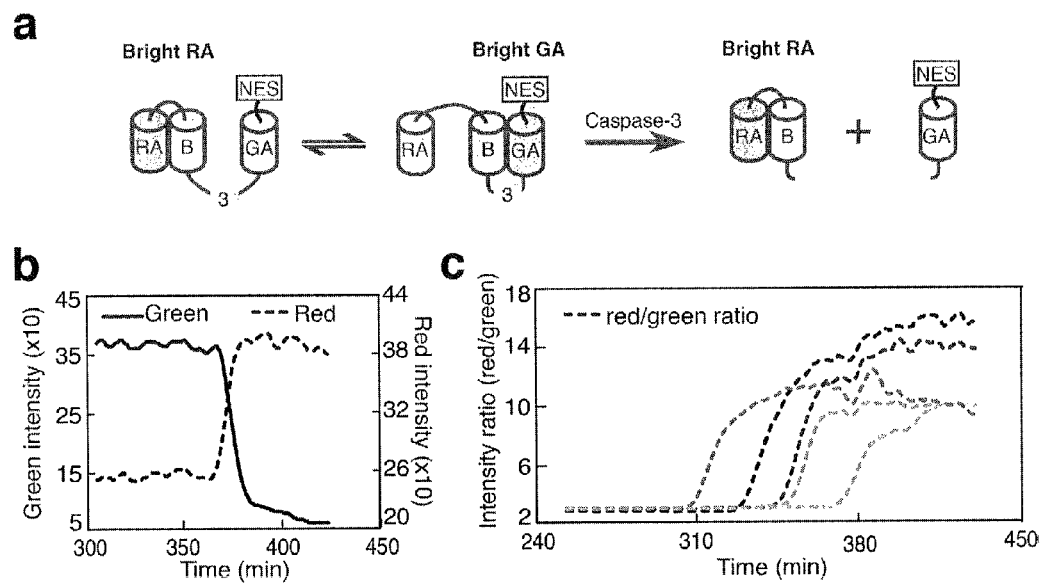
FIG. 13 shows intramolecular colour-switch FPX for imaging of caspase-3 activity.

As illustrated in FIG. 13a, a caspase-3 reporter gene which encoded RA-linker-B-DEVD-GA$^{NES}$ was constructed. The rationale behind this construct is that it would initially exhibit a combination of green and red fluorescence due to intramolecular exchange of the B copy between the two A copies. Upon cleavage of the DEVD caspase-3 substrate sequence, GA would be released and RA would be strongly preferred to bind with B due to its high effective concentration. Accordingly, green fluorescence would decrease and red fluorescence would increase.

In FIG. 13b, in which whole cell green and red intensities from imaging of HeLa cells expressing RA-linker-B-DEVD-GA$^{NES}$ and undergoing staurosporine-induced apoptosis, imaging of transfected cells undergoing staurosporine-induced apoptosis revealed that the eventual process of caspase-3 activation was associated with a rapid increase of red fluorescence and a concurrent loss of green fluorescence. FIG. 13c illustrates red-to-green intensity ratio vs. time for multiple cells treated and analyzed as in FIG. 13b. This shows that for the intramolecular construct, the baseline fluorescence ratio showed little cell-to-cell variability and a pronounced increase upon caspase cleavage. The X-axis represents time elapsed from 1 h after cells were treated with staurosporine.

Figure 14:
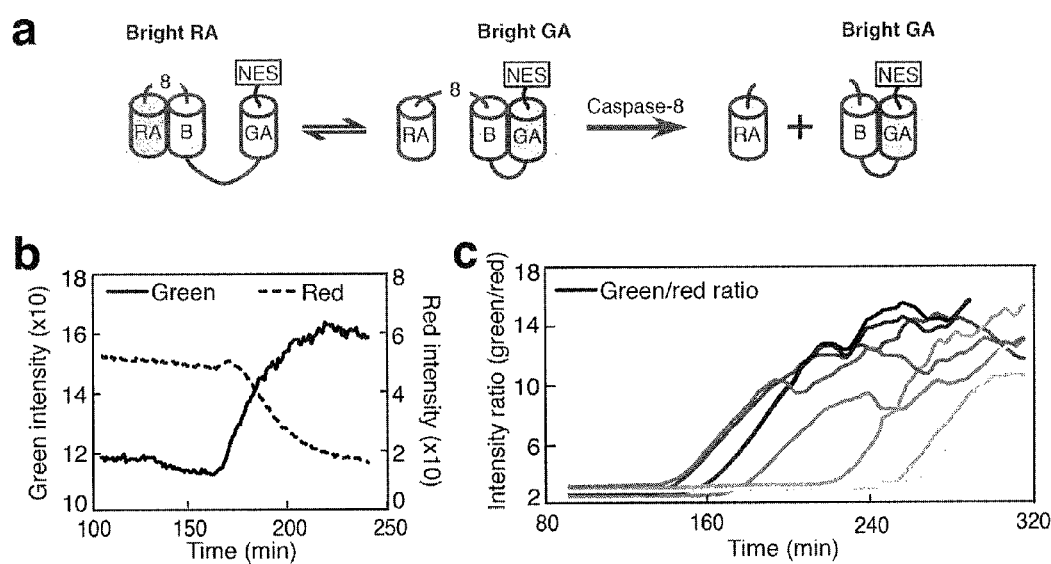
FIG. 14 shows intramolecular colour-switch FPX for imaging of caspase-8 activity.

FIG. 14 shows analogous experiments for the detection of caspase-8 activity which provided very similar results and overall conclusions regarding the robustness of this approach. FIG. 14a shows a schematic representation of a single polypeptide FPX biosensor for caspase-8. FIG. 14b shows whole cell green and red intensities from imaging of HeLa cells expressing RA-IETD-B-linker-GA$^{NES}$ and undergoing staurosporine-induced apoptosis. FIG. 14c illustrates green-to-red intensity ratio vs. time for multiple cells treated and analyzed as in FIG. 14b. The X-axis represents time elapsed from 1 h after cells were treated with staurosporine.

Figure 15:
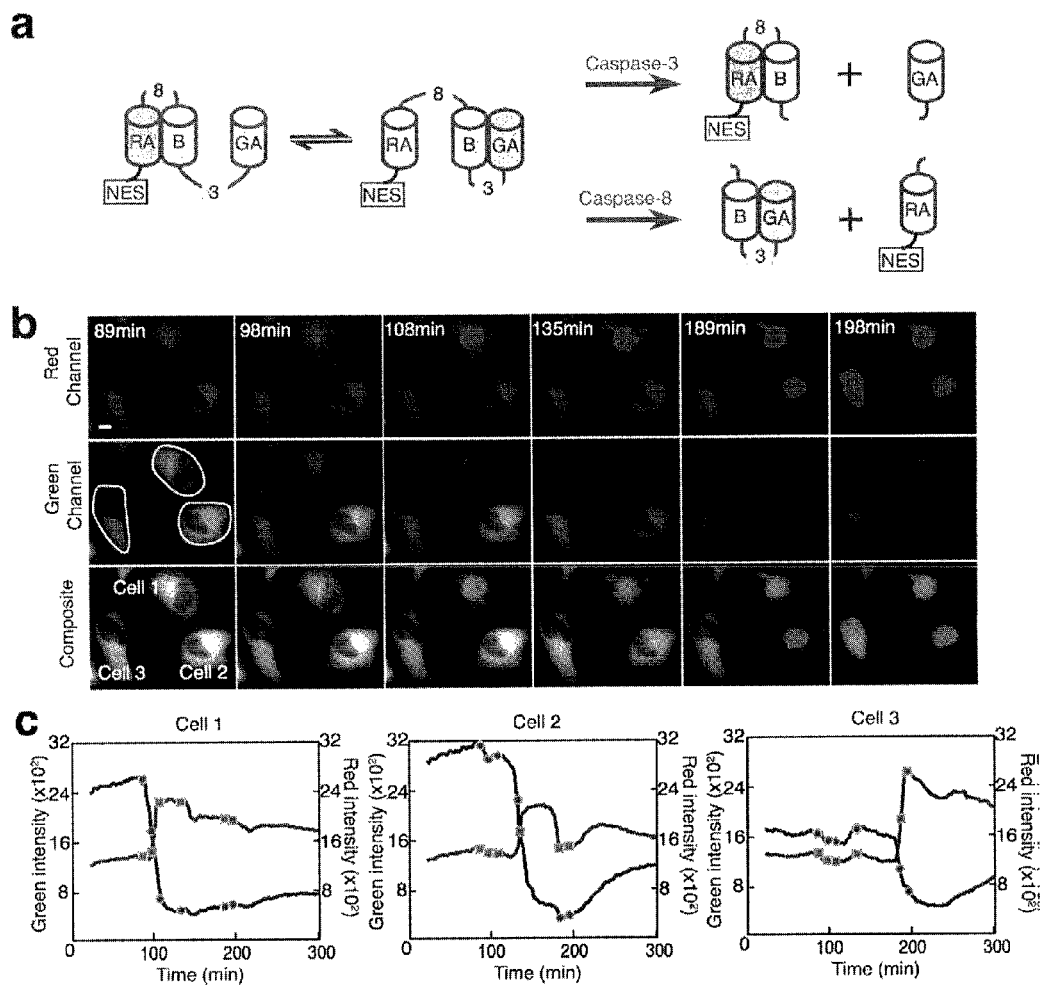
FIG. 15 shows intramolecular colour-switch FPX for imaging of caspase-3 and -8 activity.

Previous efforts to detect two caspase activities with a single polypeptide FRET-based biosensor (i.e., containing 3 FPs linked by two substrate sequences) have been tested (Wu et al., 2006; Kominami et al., 2012). A FPX biosensor for simultaneous detection of caspase-3 and caspase-8 activity was constructed. As FIG. 15a illustrates, this biosensor was a tandem heterotrimer (RA$^{NES}$-IETD-B-DEVD-GA) in which RA with an NES is linked via an IETD caspase-8 substrate to the B copy, which is in turn linked to GA via a DEVD caspase-3 substrate. As shown in FIG. 15b, which shows selected frames from imaging of HeLa cells expressing RA$^{NES}$-IETD-B-DEVD-GA and undergoing staurosporine-induced apoptosis, cells expressing RA$^{NES}$-IETDB-DEVD-GA exhibited both green and red cytoplasmic fluorescence, consistent with the expectation that both RA and GA would compete for formation of a fluorescent heterodimer with copy B. Caspase-3 catalyzed release of GA or caspase-8 catalyzed release of RA, was expected to lead to an increase in red fluorescence (and loss of green) or increase in green fluorescence (loss of red), respectively, due to decreased competition for binding to B. Accordingly, such an implementation should enable the order of caspase activation to be determined with greater confidence than the dual reporter construct strategy described herein. Scale bar represents 10 μm.

FIG. 15c shows graphs of intensity vs. time of green and red fluorescence. X-axis represents time elapsed from 1 h after cells were treated with staurosporine. Time points corresponding to the frames of green and red channel in FIG. 15b are represented as circles and squares, respectively. These data show that imaging of transfected cells undergoing staurosporine-induced apoptosis revealed that the eventual process of caspase activation was associated with a rapid increase of red fluorescence and a concurrent loss of green fluorescence. This may suggest that caspase-3 activation is occurring prior to caspase-8 activation. Following the initial rapid change, red fluorescence was observed to decrease and green fluorescence to increase, which may be due the ongoing release of RA through the action of caspase-8, which frees up more of the B copy to bind to previously released GA. Attempts to use tandem repeats of the IETD caspase-8 substrate did not result in larger increases in green fluorescence. The unique feature of the tandem heterotrimer strategy for probing multiple protease activities is that it provides a simple and robust green-to-red or red-to-green color switch depending upon which protease is activated first. This feature distinguishes this approach from alternative heterotrimeric FRET strategies where cleavage of one of the two substrates leads to more complex and typically subtle spectral changes.

Example 6: Single Color FPX with a Dark a Copy and B Copy Swapping

To enable the use of the FPX strategy in a single color implementation, a DA protein that can compete for binding to the B copy was engineered, but does not become fluorescent itself (FIG. 1c). This protein could be used in place of either GA or RA in any of the assays reported in this document, and would effectively turn the green-to-red (or vice versa) color switch into a single color "turn-on" or "turn-off" fluorescence change. Site-directed mutagenesis and library screening was used to engineer a DA protein that could compete with a fluorogenic GA or RA (RA shown in scheme) for binding to the B copy. The second residue (Tyr) of the chromophore forming tripeptide sequence of GA, Met-Tyr-Gly, was mutated to all possible amino acids using the NNK codon. Colonies were plated and nonfluorescent clones were picked. DNA sequencing of the picked clones revealed that the Tyr had been mutated to Asn, Pro, Phe, Leu, Cys in different variants. When each of these variants was purified, it was found that the clone with Asn in the second position of the chromophore (i.e., Met-Asn-Gly) gave a high yield of soluble protein and could serve as a useful competitor for either GA or RA.

Advantages of FPX Technology

As demonstrated in the examples provided herein, FPX technology is a powerful, robust, and versatile technology for detecting protein-protein interactions in live cells. For most applications, FPX provides performance that surpasses that of the most comparable implementations of ddFP, FRET, or split FP technology. Necessarily, the representative and challenging examples provided herein do not capture the full range of applications that are possible with FPX technology. However, the fact that FPX has worked so well in these initial demonstrations indicates that it has tremendous potential to become the de facto standard for engineering of live cell fluorescence assays of protein-protein interactions.

REFERENCES

Ai, H., Hazelwood, K. L., Davidson, M. W., and Campbell, R. E. (2008). Fluorescent protein FRET pairs for ratiometric imaging of dual biosensors. Nat. Methods 5, 401-403.

Alford, S. C., Abdelfattah, A. S., Ding, Y., and Campbell, R. E. (2012). A fluorogenic red fluorescent protein heterodimer. Chem. Biol. 19, 353-360.

Alford, S. C., Ding, Y., Simmen, T., and Campbell, R. E. (2012). Dimerization-Dependent Green and Yellow Fluorescent Proteins. ACS Synth. Biol. 1, 569-575.

Campbell, R. E., and Davidson, M. W. (2010). Fluorescent Reporter Proteins. In Molecular Imaging with Reporter Genes (Cambridge Univ Pr), p. 1.

Carlson, H. J., and Campbell, R. E. (2009). Genetically encoded FRET-based biosensors for multiparameter fluorescence imaging. Curr. Opin. Biotechnol. 20, 19-27.

Deheyn, D. D., Kubokawa, K., McCarthy, J. K., Murakami, A., Porrachia, M., Rouse, G. W., and Holland, N. D. (2007). Endogenous green fluorescent protein (GFP) in amphioxus. Biol. Bull. 213, 95-100.

Ghosh, I., Hamilton, A. D., and Regan, L. (2000). Antiparallel leucine zipper-directed protein reassembly: application to the green fluorescent protein. J. Am. Chem. Soc. 122, 5658-5659.

Hu, C. D., Chinenov, Y., and Kerppola, T. K. (2002). Visualization of interactions among bZIP and Rel family proteins in living cells using bimolecular fluorescence complementation. Mol. Cell 9, 789-798.

Kakar, M., Davis, J. R., Kern, S. E., and Lim, C. S. (2007). Optimizing the protein switch: altering nuclear import and export signals, and ligand binding domain. J. Control Release 120, 220-232.

Kalderon, D., Roberts, B. L., Richardson, W. D., and Smith, A. E. (1984). A short amino acid sequence able to specify nuclear location. Cell 39, 499-509.

Kerppola, T. K. (2008). Bimolecular fluorescence complementation (BiFC) analysis as a probe of protein interactions in living cells. Annu. Rev. Biophys. 37, 465-487.

Kodama, Y., and Hu, C. D. (2012). Bimolecular fluorescence complementation (BiFC): a 5-year update and future perspectives. Biotechniques 53, 285-298.

Kominami, K., Nagai, T., Sawasaki, T., Tsujimura, Y., Yashima, K., Sunaga, Y., Tsuchimochi, M., Nishimura, J., Chiba, K., Nakabayashi, J., et al. (2012). In vivo imaging of hierarchical spatiotemporal activation of caspase-8 during apoptosis. PLoS One 7, e50218.

Luo, K. Q., Yu, V. C., Pu, Y., and Chang, D. C. (2003). Measuring dynamics of caspase-8 activation in a single living HeLa cell during TNFalpha-induced apoptosis. Biochem. Biophys. Res. Commun. 304, 217-222.

Masuda, H., Takenaka, Y., Yamaguchi, A., Nishikawa, S., and Mizuno, H. (2006). A novel yellowish-green fluorescent protein from the marine copepod, Chiridius poppei, and its use as a reporter protein in HeLa cells. Gene 372, 18-25.

Matz, M. V., Fradkov, A. F., Labas, Y. A., Savitsky, A. P., Zaraisky, A. G., Markelov, M. L., and Lukyanov, S. A. (1999). Fluorescent proteins from nonbioluminescent Anthozoa species. Nat. Biotechnol. 17, 969-973.

Michnick, S. W., Ear, P. H., Manderson, E. N., Remy, I., and Stefan, E. (2007). Universal strategies in research and drug discovery based on protein-fragment complementation assays. Nat Rev Drug Discov 6, 569-582.

Miyawaki, A., Llopis, J., Heim, R., McCaffery, J. M., Adams, J. A., Ikura, M., and Tsien, R. Y. (1997). Fluorescent indicators for Ca2+ based on green fluorescent proteins and calmodulin. Nature 388, 882-887.

Nyfeler, B., Michnick, S. W., and Hauri, H. P. (2005). Capturing protein interactions in the secretory pathway of living cells. Proc. Natl. Acad. Sci. U.S.A. 102, 6350-6355.

Shaner, N. C., Lambert, G. G., Chammas, A., Ni, Y., Cranfill, P. J., Baird, M. A., Sell, B. R., Allen, J. R., Day, R. N., Israelsson, M., et al. (2013). A bright monomeric green fluorescent protein derived from Branchiostoma lanceolatum. Nat. Methods 10, 407-409.

Shimomura, O., Johnson, F. H., and Saiga, Y. (1962). Extraction, Purification and Properties of Aequorin, a Bioluminescent Protein from Luminous Hydromedusan, Aequorea. J. Cell. Comp. Physiol. 59, 223-239.

Thornberry, N. A., Rano, T. A., Peterson, E. P., Rasper, D. M., Timkey, T., Garcia-Calvo, M., Houtzager, V. M., Nordstrom, P. A., Roy, S., Vaillancourt, J. P., et al. (1997). A combinatorial approach defines specificities of members of the caspase family and granzyme B. Functional relationships established for key mediators of apoptosis. J. Biol. Chem. 272, 17907-17911.

Wen, W., Meinkotht, J. L., Tsien, R. Y., and Taylor, S. S. (1995). Identification of a signal for rapid export of proteins from the nucleus. Cell 82, 463-473.

Wu, X., Simone, J., Hewgill, D., Siegel, R., Lipsky, P. E., and He, L. (2006). Measurement of two caspase activities simultaneously in living cells by a novel dual FRET fluorescent indicator probe. Cytometry A 69, 477-486.

Xu, X., Gerard, A. L., Huang, B. C., Anderson, D. C., Payan, D. G., and Luo, Y. (1998). Detection of programmed cell death using fluorescence energy transfer. Nucleic Acids Res. 26, 2034-2035.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method of assaying a molecular process, comprising the steps of:
   a) providing an exchange proteins and a first signalling proteins, wherein the exchange proteins interacts with the first signalling proteins to form a first complex,
   b) introducing a second signalling protein, wherein in response to the molecular process, the exchange protein dissociates from the first signalling protein in the first complex and associates with the second signalling proteins to form a second complex, and
   c) measuring change in signal generated, thereby assaying the molecular process, wherein each of the first signalling protein, the second signaling proteins, and the exchange protein are dimerization dependent fluorescent proteins (ddFPs) and wherein one of the first signalling protein and second signalling protein is a red ddFP, and the other is a green ddFP.

2. The method of claim 1, wherein the molecular process is a loss of protein-protein interaction or physical connection.

3. The method of claim 1, wherein the change in signal is a change in fluorescence intensity, a change in fluorescence color, or a change in subcellular localization.

4. The method of claim 1, wherein the change in signal generated fluorescence is a green-to-red or red-to-green change in fluorescence color.

5. The method of claim 1, wherein the exchange, first or second proteins are conjugated with one or more further proteins.

6. The method of claim 5, wherein the one or more further proteins interact with each other, or dissociate from each other, thereby changing the signal.

7. The method of claim 1, wherein an enzyme catalyzes the interaction or loss of interaction between signalling proteins.

8. The method of claim 1, wherein the proteins are located in a cell.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
```

```
-continued

<220> FEATURE:
<223> OTHER INFORMATION: Caspase-3 substrate sequence

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: caspase-8 substrate sequence

<400> SEQUENCE: 2

Ile Glu Thr Asp
1

<210> SEQ ID NO 3
<211> LENGTH: 4
<212> TYPE: PRT
<213> ORGANISM: Artificial Sequence
<220> FEATURE:
<223> OTHER INFORMATION: caspase-9 substrate sequence

<400> SEQUENCE: 3

Leu Glu His Asp
1
```